United States Patent [19]
Andersson et al.

[11] Patent Number: 5,936,061
[45] Date of Patent: Aug. 10, 1999

[54] USE OF HYDROPHOBIC ZEOLITES, SYRINGE AND METHOD FOR REMOVING OF PRESERVATIVES FROM A POLYPEPTIDE SOLUTION

[76] Inventors: Sten Andersson, Södra Långgatan 27, S-380 74 Löttorp; Håkan Eriksson, Borgåslingan 12, S-224 72 Lund; Kåre Larsson, Norra Villavägen 7B, S-237 34 Bjärred, all of Sweden

[21] Appl. No.: 09/051,752

[22] PCT Filed: Oct. 15, 1996

[86] PCT No.: PCT/SE96/01306

§ 371 Date: Apr. 20, 1998

§ 102(e) Date: Apr. 20, 1998

[87] PCT Pub. No.: WO97/15391

PCT Pub. Date: May 1, 1997

[30] Foreign Application Priority Data

Oct. 24, 1995 [SE] Sweden .................................. 9503731

[51] Int. Cl.⁶ .................................................. A61K 37/00
[52] U.S. Cl. ...................... 530/305; 530/412; 530/415; 530/416; 530/427; 210/679; 210/690; 210/691; 604/27; 604/36; 604/187; 604/190
[58] Field of Search ................... 530/305, 412, 530/415, 416, 427; 210/679, 690, 691; 604/27, 36, 187, 190

[56] References Cited

U.S. PATENT DOCUMENTS

| | | | |
|---|---|---|---|
| 4,240,986 | 12/1980 | Priegnitz | 568/937 |
| 5,108,617 | 4/1992 | Eriksson et al. | 210/679 |
| 5,314,855 | 5/1994 | Thorpe et al. | 502/80 |
| 5,788,662 | 8/1998 | Antanavich et al. | 604/6 |

FOREIGN PATENT DOCUMENTS

| | | |
|---|---|---|
| 0021267 | 1/1981 | European Pat. Off. . |
| WO 94/00213 | 1/1994 | WIPO . |

OTHER PUBLICATIONS

*Ion Exchangers in Analytical Chemistry*, Olof Samuelson, John Wiley & Sons, Inc., New York, pp. 231–243. No Year Given.

Primary Examiner—Cecilia J. Tsang
Assistant Examiner—C. Delacroix-Muirheid
Attorney, Agent, or Firm—Burns, Doane, Swecker & Mathis, L.L.P.

[57] ABSTRACT

A new use of hydrophobic zeolites, viz. for removing preservatives from (poly)peptide solutions, e.g. solutions of pharmaceutical preparations. The use is of particular interest in connection with protein solutions, especially insulin solutions. The invention further relates to an injection syringe for such solutions, in which syringe a zeolite of the type at issue is placed for contact with the solution to remove preservatives therefrom.

31 Claims, 3 Drawing Sheets

USE OF HYDROPHOBIC ZEOLITES, SYRINGE AND METHOD FOR REMOVING OF PRESERVATIVES FROM A POLYPEPTIDE SOLUTION

FIELD OF THE INVENTION

The present invention relates to a new use of hydrophobic zeolites, i.e. to remove preservatives from (poly)peptide solutions. The invention further relates to a new product intended for injection solutions, more specifically a syringe intended for such solutions, which contains said hydrophobic zeolite for removing preservatives from the injection solution.

BACKGROUND OF THE INVENTION

Pharmaceutical preparations intended for injection are usually supplied as prepared injection solutions for immediate use. In many cases, such pharmaceutical preparations consist of proteins, the solutions of which cannot be heat sterilised. For this reason, effective preservatives are generally added to the solutions, which in turn means that the preservative is also injected into the patients. If this preservative could be removed, the patient would be spared toxic exposure, which must be considered particularly serious when the pharmaceutical preparation is used constantly. One example in this respect is diabetics injecting insulin, and the prevalent product on the market contains phenol as preservative. Another example is somatropin, where two dominating manufacturers use m-cresol as preservative and a third uses benzyl alcohol. It is also common for manufacturers of this type of drugs to supply special disposable syringes with dose indicator.

Especially for the last-mentioned reason, i.e. that the drugs are supplied in special disposable syringes, more or less complicated methods for removing the preservative cannot be applied. The present invention offers on the other hand a very simple but at the same time very effective method for removing preservatives from such solutions, the method being so simple that it can even be applied in connection with disposable syringes of the type involved. According to the present invention, it has thus been found that hydrophobic zeolites can be used for this purpose in a very simple, quick and effective manner. The fact that the invention is at the same time surprising is illustrated by the following.

The use of zeolites for adsorption of some specific types of organic compounds is per se known. Thus, e.g. U.S. Pat. No. 5,108,617 discloses the use of hydrophobic zeolites for adsorption of detergents from a solution containing the same, while PCT Application SE93/00582 discloses the use of hydrophobic zeolites for adsorption of hydrophobic proteins or peptides. However, none of these publications indicates that such hydrophobic zeolites could be usable for efficient removing of the type of compounds that is intended according to the present invention, viz. preservatives from (poly)peptide solutions, for instance solutions of pharmaceutical products. Moreover it is particularly surprising that the invention has been found to function extremely well for purifying solutions containing peptides or proteins, since, as mentioned above, hydrophobic zeolites have been used precisely to adsorb peptides or proteins.

DESCRIPTION OF THE INVENTION

A first aspect of the invention thus concerns a new use of hydrophobic zeolites, i.e. for removing preservatives from a (poly)peptide solution containing the same. In most cases, a water-based solution is involved, especially a solution of a pharmaceutical preparation, but also other types of solutions, for instance all sorts of biomedical solutions, containing similar preservatives are, of course, possible in connection with the use according to the invention.

As will be evident from the following, an extremely interesting embodiment of the invention is the use for a protein solution. However, the inventive idea should be applicable to all types of peptides, i.e. anything from peptides having a few amino acids bound to each other (e.g. oligopeptides having at most about 10 amino acids bound to each other) via polypeptides having up to about 100 amino acids, and up to polypeptides having more than about 100 amino acids, in which case the polypeptides usually change to be called proteins. The term (poly)peptide should thus, in connection with the invention, be interpreted as a common term for peptides (including oligopeptides) and polypeptides (including proteins).

The use according to the invention can in practical terms take place according to principles that are per se known, which generally means that the solution involved is contacted with an efficient hydrophobic zeolite, in which case such an amount thereof is used that the desired degree of adsorption of the preservative to the zeolite is achieved. This degree of adsorption can, of course, vary from application to application, and therefore no specific degree of adsorption can be generally stated. It is, however, in many cases a matter of removing at least 80%, more preferred at least 90%, and most preferred at least 95% or even at least 98% or still more of the preservative present.

Although a specific embodiment of the invention will now be described in connection with a syringe intended for injection solutions, the use according to the invention can in general take place in batches as well as continuously or semicontinuously. In an alternative, the hydrophobic zeolite is added directly to the solution, whereas another alternative is represented by the case where the hydrophobic zeolite is packed in a column or the like, through which the solution to be purified is allowed to pass. Various specific applications of these alternatives are, of course, possible, but these need not be described in more detail here since they can be obtained from the per se known technique.

The use according to the invention is, as mentioned above, particularly advantageous in connection with solutions of pharmaceutical preparations or other biomedical solutions and, especially, in connection with injection solutions.

The use according to the invention for purifying protein solutions is of particular interest, where it has been found extremely efficient although hydrophobic zeolites have previously been used for adsorption of precisely proteins. A relevant embodiment is use of the invention for insulin solutions, especially in consideration of the fact that such solutions are often supplied in the form of special disposable syringes having a dose indicator. Other proteins of interest, to which the invention can be applied, are somatropin and growth hormone (GH).

In the embodiment of the invention where the solution is present in a syringe, which in most cases is a disposable syringe, the hydrophobic zeolite is suitably placed in the syringe, thereby forcing the solution to come into contact with the zeolite before it is injected into the patient.

A particularly preferred embodiment of this aspect of the invention is represented by the case where the zeolite is placed in the bottom of the syringe, since this renders it possible to use the zeolite such that the solution is forced to pass therethrough, both when the syringe is being filled and when it is being emptied. Different arrangements in respect of the placing of the zeolite may be involved, but a preferred embodiment is a syringe in which the zeolite is fixed to the bottom in the form of filter, e.g. a sintered filter. A further variant is represented by a filter of some other type, where the zeolite is arranged on top of this filter in the form of a granulate or the like.

The zeolite used is preferably of the type corresponding to the general basic structure

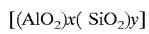

wherein x and y are integers and y/x>15. A zeolite of the formula at issue is especially preferred, wherein y/x>100, more preferred >900.

Hydrophobic zeolites of the type as stated are selected according to the invention preferably from the group consisting of silicalite, mordenite and zeolite Y, zeolite Y being especially preferred.

Otherwise, per se known principles apply to the zeolite. Thus, a cation can be bound to the zeolitic basic structure for each Al atom, for instance Na. Other ions, such as P, B and Ge can to some extent replace Al and Si to provide zeolitic basic structures and can thus also be utilised in the use of the invention. All zeolites contain a certain amount of water molecules. Hydrophobic zeolites are usually prepared by modification of synthetically derived hydrophilic zeolites, from which a greater or smaller amount of the Al molecules has been removed to make the zeolite hydrophobic.

The pore size of the zeolites at issue is usually in the range 3–10 Å and the accessibility to the pore system is dimensionally dependent. For zeolite Y and mordenite, it is a matter of a pore size in the upper range, viz. about 7.0–7.5 Å, while silicalite is a zeolite having a pore size of about 5.5 Å. The pore system of zeolite Y and silicalite is easily accessible depending on the three-dimensional arrangement of the channels, whereas mordenite has a one-dimensional pore system.

Zeolites having a large amount of silicon or silica have strongly hydrophobic properties and are stable in water-based system within a wide pH range and are besides insensitive to oxidising and reducing agents. Moreover, they resist high pressures and high temperatures without any changes.

Any risks of chemical contamination and biological infection can be eliminated by pretreatment of the zeolite. Besides zeolites can easily be regenerated. Another preferred embodiment of the invention is therefore represented by the case in which the zeolite is pretreated or prepurified, for instance by heating to a high temperature. This is usually a temperature above 700° C., preferably above 850° C. and most preferred in the range 900–1100° C. Another alternative prepurifying method involves treatment of the zeolite with so-called super-critical carbon dioxide.

Moreover, the zeolite can be used as such or in the form of sintered zeolite crystals or in the form of crystals enclosed or suspended in non-zeolitic materials. It may also be deposited on, or in some other suitable manner be combined with one or more, preferably permeable, non-zeolitic materials. An example of usable non-zeolitic materials is agarose.

The chemistry of zeolites is besides well known to those skilled in the art and therefore need not be described in detail here. Further details regarding the use of zeolites for purification or adsorption purposes can thus be obtained from the prior art, especially the above-mentioned publications.

The hydrophobic zeolites are generally seen usable for removing various, more or less toxic preservatives in solutions of the above-mentioned type. A group of preservatives for which the use according to the invention is especially relevant is, however, the preservatives used in connection with drugs for producing sterile injection solutions, for instance for proteins, such as insulin. The most common preservatives in these contexts, for which the invention should function, are phenol, cresol (especially m-cresol), benzyl alcohol, benzalkonium chloride, cetrimide, chlorobutanol, chlorhexidine, chlorcresol, hydroxybenzoates, phenethyl alcohol, phenoxyethanol and phenylmercuric nitrate. Above all, the removal of especially phenol and cresol as preservative in insulin solutions represents a particularly preferred embodiment of the invention because of the large number of diabetics who inject themselves with insulin several times a day, and where toxic exposure to preservatives is an adverse side-effect which could not be eliminated up to now.

The invention, however, is not limited to the removal of preservatives merely from injection solutions or even solutions of drugs, but can be used also in other contexts where preservatives are present, for instance in other biomedical contexts.

The adsorption of preservatives by means of the hydrophobic zeolites according to the present invention is extremely rapid and efficient. At an optimum ratio of zeolite to preservative, it is a matter of seconds rather than minutes for removing a preservative. In respect of optimisation, zeolites generally adsorb molecules of the preservative based on the pore size of the actual zeolite structure. This optimisation as well as optimisation of the amount required in every individual case to achieve the desired effect are, however, completely within the scope of what an expert can determine from simple tests. However, the amount of preservative that is to be adsorbed usually is less than 1% of the weight of the zeolite.

As mentioned above, an especially preferred embodiment of the invention is represented by the case where the hydrophobic zeolites are used to purify injection solutions, e.g. insulin solutions. Such solutions are injected by means of an injection syringe, which usually is a disposable syringe with dose indicator, and according to a second aspect of the invention, it concerns such a syringe as comprises an active hydrophobic zeolite as defined above, adapted to come into contact the injection solution for removing the preservative therefrom.

A preferred embodiment of such a syringe is a syringe, in which the zeolite is placed in the bottom of the syringe, since this means that the injection solution is caused to pass through the zeolite both when sucking-in the solution into the syringe and during the actual injection.

The arrangement of the zeolite in the syringe may vary, but a preferred variant is represented by the case in which the zeolite is present in the form of a filter, e.g. a sintered filter of the zeolite at issue. A further alternative is to arrange a filter of some other kind, e.g. a microfilter, in the syringe and on top of this arrange the zeolite in the form of a granulate or the like.

The injection syringe is otherwise built according to known principles and therefore need not be described in more detail here.

BRIEF DESCRIPTION OF THE DRAWINGS

FIG. 4 illustrates more concretely an injection syringe comprising a cylinder 1, to the bottom 2 of which a needle 3 is fixed. The cylinder 1 comprises in conventional manner a piston 4 and its associated piston rod 5. In the case illustrated, the cylinder 1 is filled with an injection solution 6 in the space between the piston 4 and the bottom 2. In the embodiment shown, an elongate zeolite filter 7 is arranged inside the needle 3 of the syringe.

FIG. 5 illustrates a syringe of exactly the same composition as in FIG. 4, i.e. the reference numerals have the same meaning as in FIG. 4, but a zeolite filter 8 is arranged in a projecting part 9 of the bottom of the cylinder 1.

Figure 4:
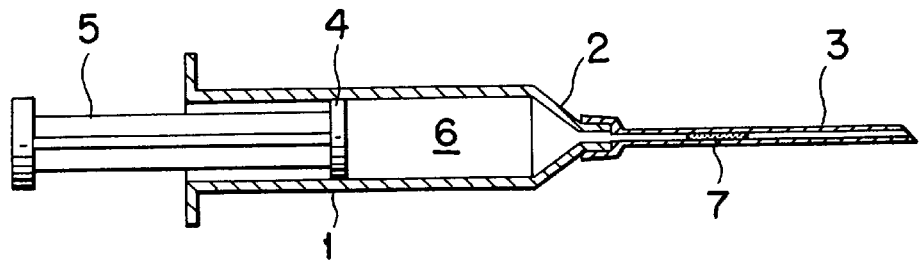
FIG. 4 shows an embodiment in cross-section of the syringe according to the invention, the zeolite being placed in the tip of the syringe.
Figure 5:
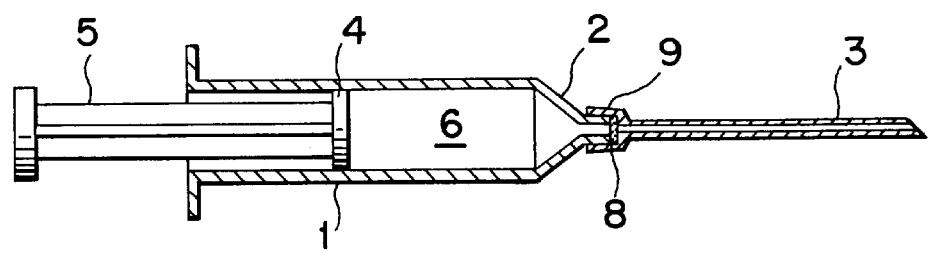
FIG. 5 shows a further embodiment in cross-section of the syringe according to the invention, the zeolite being placed in the bottom of the syringe.
Figure 6:
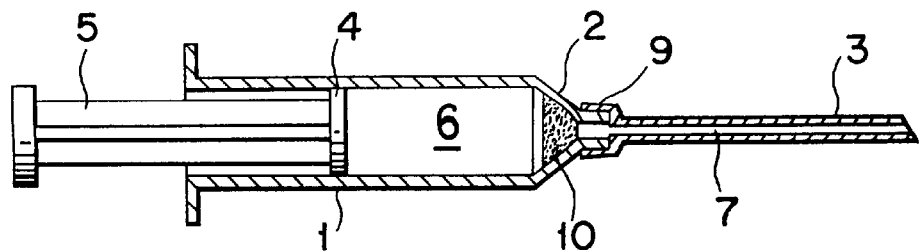
FIG. 6 shows an alternative embodiment in cross-section of the syringe according to the invention, the zeolite being placed in the bottom of the syringe in a different manner.

Finally, in FIG. 6 the reference numerals are also the same as in FIG. 4, but in this case a zeolite filter 10 is arranged in the bottom 2 of the cylinder 1.

In all three cases, the injection syringe is handled in conventional manner in respect of filling the syringe with injection solution and injecting said solution into an individual, and therefore this need not be described in more detail here. The novel matter in the context, however, is the arrangement of a zeolite filter 7, 8, 10, in such a manner that the injection solution and the preservative added pass through the filter on the occasion of suction as well as injection, which renders an effective removal of the preservative possible.

EXAMPLES

The present invention will now be further illustrated by means of the following concrete Examples, which are merely intended to illustrate the invention and therefore should not be considered restrictive to the same in any respect other than what is evident from the accompanying claims.

By way of introduction, the following concrete background of the invention can be given. When studying the zeolite binding of other hydrophobic molecules, we found unexpectedly that zeolite Y could remove phenol extremely efficiently from insulin solutions containing glycerol, which substance is present in insulin solutions to give them the correct osmotic equilibrium. Phenol is, by its typical smell, easy to identify down to low concentrations. Our first observation was that an addition of 10 mg zeolite Y/ml Insulatard® (a commercial insulation solution for direct injection) almost completely eliminated the smell of phenol in spite of the presence of insulin. Later analyses have shown that the insulin and glycerol levels are affected marginally only.

Example 1
Adsorption of phenol to hydrophobic zeolite Y.

Phenol (0.65 mg/ml) dissolved in 20 mM phosphate buffer pH 7 with 16 mg glycerol/ml and 5 mg bovine serum albumin (BSA)/ml are added to varying amounts of hydrophobic zeolite Y. The samples are Vortex-mixed for 30 s and the zeolite is separated from the solution by centrifugation 13000×g for 10 min. The amount of phenol that remains in the solution after incubation with zeolite is analysed by HPLC.

Figure 1:
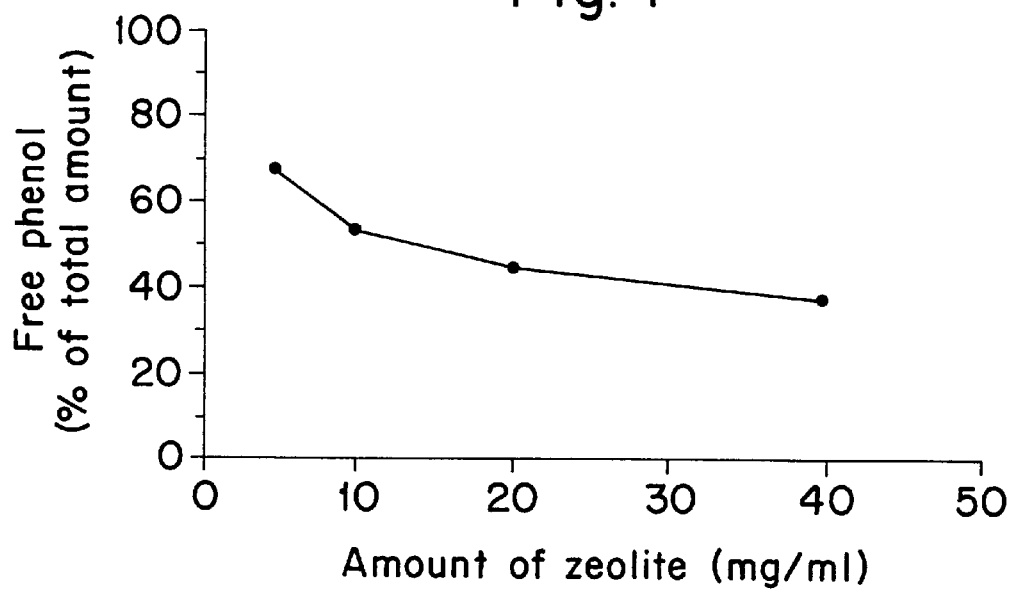
FIG. 1 shows the results of adsorption experiments with zeolite Y as described in Example 1, with the amount of remaining phenol plotted against the amount of zeolite.

The results are presented in FIG. 1.

Example 2
Adsorption of m-cresol to hydrophobic zeolite Y.

m-cresol (1.5 mg/ml) dissolved in 20 mM phosphate buffer pH 7 with 16 mg glycerol/ml and 5 mg BSA/ml are added to varying amounts of hydrophobic zeolite Y. The samples are Vortex-mixed for 30 s and the zeolite is separated from the solution by centrifugation 13000×g for 10 min. The amount of m-cresol that remains in the solution after incubation with zeolite is analysed by HPLC.

Figure 2:
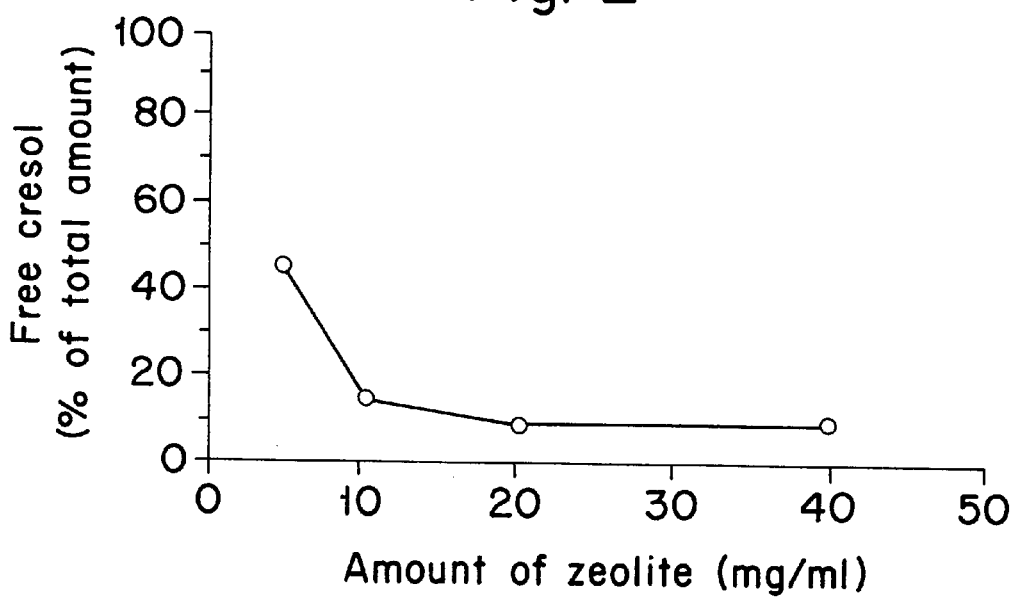
FIG. 2 shows the results of adsorption experiments with zeolite Y as described in Example 2, with the amount of remaining m-cresol plotted against the amount of zeolite.

The results are shown in FIG. 2.

Example 3
Adsorption of a mixture of phenol and m-cresol to hydrophobic zeolite Y.

Phenol (0.65 mg/ml), m-cresol (1.5 mg/ml) dissolved in 20 mM phosphate buffer pH 7 with 16 mg glycerol/ml and 5 mg BSA/ml are added to varying amounts of hydrophobic zeolite Y. The samples are Vortex-mixed for 30 s and the zeolite is separated from the solution by centrifugation 13000×g for 10 min. The amount of phenol and m-cresol remaining in the solution after incubation with zeolite is analysed by HPLC.

Figure 3:
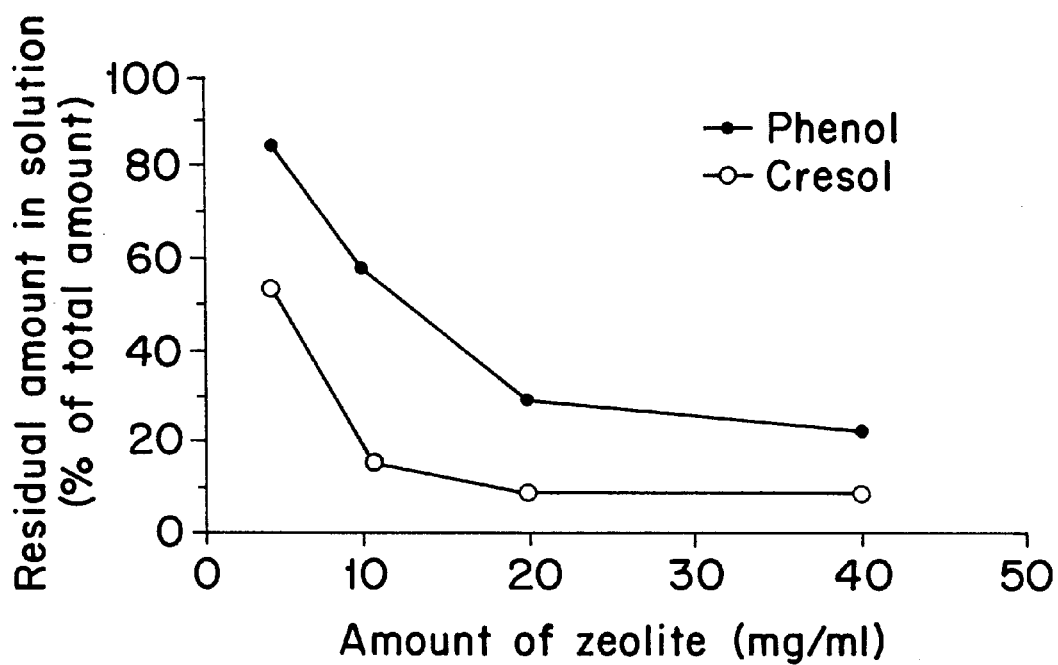
FIG. 3 shows the results of adsorption experiments with zeolite Y as described in Example 3, with the amount of remaining phenol+m-cresol plotted against the amount of zeolite.

The results are shown in FIG. 3.

Example 4
Adsorption of phenol to hydrophobic zeolite Y packed in a syringe.

In a 2 ml syringe without piston, varying amounts of hydrophobic zeolite Y are packed between two 20 µm filter frits. After the syringe, a 0.45 µm filter is connected, and phenol 0.65 mg/ml in 20 mM phosphate buffer pH 4.6 with 16 mg glycerol/ml is pressed through the syringe by the piston. On the filtrate, the absorbance at 280 nm is measured for determining the phenol content after contacting the zeolite.

The results are shown in Table 1 below.

TABLE 1

| Amount of zeolite Y mg/ml phenol solution | Phenol content after syringe | |
|---|---|---|
| | mg/ml | % of original concentration |
| 100 | 0.007 | 1.0 |
| 50 | 0.003 | 0.5 |
| 25 | 0.51 | 79 |
| 12.5 | 0.59 | 90 |

Here follow some comments on the above Examples.

Examples 1 and 2 are carried out as batch testings only and yield no total adsorption. However, the adsorption will probably be improved if the zeolite is packed, for instance, in a syringe in which a column effect is obtained, which is indicated in Example 4. It should also be noted that the adsorption is improved when phenol and cresol are present simultaneously (see Example 3).

Unfortunately, phenol and cresol interfere with the analysis of protein. When adding 40 mg/ml of zeolite (see FIGS.

2 and 3), the cresol and phenol content is so low that the determinations of protein become reliable. The measurements then demonstrated that the protein loss was negligible (approximately below a few per cent).

We claim:

1. A process for removing a preservative from a (poly) peptide solution, comprising contacting said (poly)peptide solution with an amount of a hydrophobic zeolite effective to achieve the desired degree of adsorption of said preservative to said zeolite.

2. The process according to claim 1, wherein the solution is a water-based (poly)peptide solution.

3. The process according to claim 1, wherein the solution is a protein solution.

4. The process according to claim 1, wherein the solution is a solution of a pharmaceutical preparation.

5. The process according to claim 4, wherein the solution of the pharmaceutical preparation is an injection solution.

6. The process according to claim 3, wherein the protein solution is an insulin solution.

7. The process according to claim 3, wherein the protein solution is a solution of somatropin or growth hormone (GH).

8. The process according to claim 1, wherein the zeolite is a zeolite of the basic structure

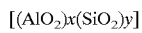

[$(AlO_2)x(SiO_2)y$]

wherein x and y are integers and y/z>15.

9. The process according to claim 8, wherein, in the stated basic structure, y/x>100.

10. The process according to claim 8, wherein, in the stated basic structure, y/x>900.

11. The process according to claim 8, wherein the zeolite is selected from the group consisting of silicalite, mordenite and zeolite Y.

12. The process according to claim 11, wherein the zeolite essentially consists of zeolite Y.

13. The process according to claim 1, wherein the zeolite is prepurified by heating to a temperature above 700° C.

14. The process according to claim 1, wherein the zeolite is prepurified by heating to a temperature above 850° C.

15. The process according to claim 1, wherein the zeolite is prepurified by heating to a temperature in the range of 900–1100° C.

16. The process according to claim 1, wherein the zeolite is prepurified by treatment with supercritical carbon dioxide.

17. The process according to claim 1, wherein the preservative is a preservative additive used in connection with pharmaceutical preparations and/or biomedicine.

18. The process according to claim 17, wherein the preservative is a preservative used for injection solutions in connection with pharmaceutical preparations.

19. The process according to claim 1, wherein the preservative is selected from the group consisting of phenol, cresol, benzyl alcohol, benzalkonium chloride, cetrimide, chlorobutanol, chlorhexidine, chlorcresol, hydroxybenzoates, phenethyl alcohol, phenoxyethanol and phenylmercuric nitrate.

20. The process according to claim 19, wherein the preservative is phenol and/or cresol.

21. The process according to claim 19, wherein the preservative is m-cresol.

22. The process according to claim 5, wherein the solution is present in a syringe, said zeolite being placed in the syringe such that the solution is contacted with the zeolite before the solution is used for injection purposes.

23. The process according to claim 22, wherein the syringe is a disposable syringe.

24. The process according to claim 22, wherein the zeolite is placed in the bottom of the syringe.

25. The process according to claim 24, wherein the zeolite is in the form of a filter.

26. The process according to claim 1, wherein the zeolite is packed in a column.

27. A syringe for an injection solution, said syringe comprising a hydrophobic zeolite effective for adsorbing a preservative from a (poly)peptide solution, said zeolite adapted to come into contact with the injection solution for removing a preservative therefrom.

28. The syringe according to claim 27, wherein the injection solution is a protein solution.

29. The syringe according to claim 27, wherein the injection solution is an insulin solution.

30. The syringe according to claim 27, wherein the zeolite is placed in the bottom of the syringe.

31. The syringe according to claim 27, wherein the zeolite is in the form of a filter.

* * * * *